(12) United States Patent
Friedman (10) Patent No.: US 8,142,497 B2
(45) Date of Patent: *Mar. 27, 2012

(54) SUTURELESS HEART VALVE ATTACHMENT (75) Inventor: Robert Friedman, Los Angeles, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 57 days.

This patent is subject to a terminal disclaimer.

(21) Appl. No.: 12/463,995

(22) Filed: May 11, 2009

(65) Prior Publication Data
US 2009/0222084 A1    Sep. 3, 2009

Related U.S. Application Data (63) Continuation of application No. 11/542,087, filed on Oct. 2, 2006, now Pat. No. 7,534,261.

(51) Int. Cl.
*A61F 2/24* (2006.01)
(52) U.S. Cl. ...................................................... 623/2.38
(58) Field of Classification Search .................. 623/1.13, 623/2.1–2.38
See application file for complete search history.

(56) References Cited

U.S. PATENT DOCUMENTS

| | | | |
|---|---|---|---|
| 4,172,295 A * | 10/1979 | Batten .......................... | 623/2.15 |
| 5,397,346 A * | 3/1995 | Walker et al. ................. | 623/2.41 |
| 5,554,185 A | 9/1996 | Block et al. | |
| 5,951,600 A | 9/1999 | Lemelson | |
| 6,143,025 A | 11/2000 | Stobie et al. | |
| 6,273,875 B1 | 8/2001 | Siman et al. | |
| 6,287,339 B1 | 9/2001 | Vazquez et al. | |
| 6,458,156 B1 | 10/2002 | Wan et al. | |
| 6,585,766 B1 | 7/2003 | Huynh et al. | |
| 6,719,790 B2 | 4/2004 | Brendzel et al. | |
| 6,730,118 B2 | 5/2004 | Spenser et al. | |
| 6,790,229 B1 | 9/2004 | Berreklouw | |
| 6,958,076 B2 * | 10/2005 | Acosta et al. ................. | 623/1.24 |

(Continued)

FOREIGN PATENT DOCUMENTS

| WO | WO 03/096932 | 11/2003 |
|---|---|---|
| WO | WO 2007/081820 | 7/2007 |

OTHER PUBLICATIONS

*PCT International Search Report for Application No. PCT/US2007/078796 dated Jul. 17, 2008.

*Primary Examiner* — Suzette J Gherbi
(74) *Attorney, Agent, or Firm* — AnneMarie Kaiser; Guy L. Cumberbatch (57) ABSTRACT

A prosthetic heart valve having spaced apart anchoring flanges that change shape when the valve is implanted and contact the surrounding annulus to prevent migration of the valve. The heart valve may be non-expandable and the anchoring flanges may provide the primary anchoring structure of the valve. Alternatively, the valve may be expandable wherein the anchoring flanges supplement the inherent anchoring capacity of the valve structure. The anchoring flanges are at least partly made of a material that increases in size, i.e., swells, due to absorption of body fluids. For instance, the anchoring flanges may be formed of an inner material that swells upon contact with body fluids enclosed by a cover. The anchoring flanges may be provided on an anchoring sleeve that changes shape to provide the spaced apart annular flanges for securing the valve around a fibrous annulus. An anchoring sleeve for a prosthetic heart valve having an expandable frame surrounds a majority of the frame and may define an external hourglass configuration.

25 Claims, 5 Drawing Sheets

U.S. PATENT DOCUMENTS

| | | |
|---|---|---|
| 7,011,094 B2 * | 3/2006 | Rapacki et al. .......... 128/207.15 |
| 2005/0033344 A1 * | 2/2005 | Dillard et al. ................ 606/191 |
| 2005/0137687 A1 | 6/2005 | Salahieh et al. |
| 2005/0220882 A1 | 10/2005 | Pritchard et al. |
| 2006/0004442 A1 | 1/2006 | Spenser et al. |
| 2006/0195185 A1 | 8/2006 | Lane et al. |

\* cited by examiner

SUTURELESS HEART VALVE ATTACHMENT

RELATED APPLICATIONS

The present application is a continuation of co-pending application Ser. No. 11/542,087, filed Oct. 2, 2006, entitled "SUTURELESS HEART VALVE ATTACHMENT.

FIELD OF THE INVENTION

The present invention relates generally to medical devices, and more particularly to a heart valve having anchoring flanges that change shape when implanted to anchor the valve without the use of sutures.

BACKGROUND OF THE INVENTION

Heart valve disease continues to be a significant cause of morbidity and mortality, resulting from a number of ailments including rheumatic fever and birth defects. Recent statistics show that valvular heart disease is responsible for nearly 20,000 deaths each year in the United States, and is a contributing factor in approximately 42,000 deaths. Currently, the primary treatment of aortic valve disease is valve replacement. Worldwide, there are approximately 300,000 heart valve replacement surgeries performed annually.

Two primary types of "conventional" heart valve replacements or prostheses are known. One is a mechanical-type heart valve that uses a ball and cage arrangement or a pivoting mechanical closure supported by a base structure to provide unidirectional blood flow, such as shown in U.S. Pat. No. 6,143,025 to Stobie, et al. and U.S. Pat. No. 6,719,790 to Brendzel, et al., the disclosures of which is hereby expressly incorporated by reference. The other is a tissue-type or "bioprosthetic" valve having flexible leaflets supported by a base structure and projecting into the flow stream that function much like those of a natural human heart valve and imitate their natural flexing action to coapt against each other and ensure one-way blood flow. One example of a flexible leaflet valve is disclosed in U.S. Pat. No. 6,585,766 to Huynh, et al., the disclosure of which is hereby expressly incorporated by reference.

Conventional heart valve surgery is an open-heart procedure that is highly invasive, resulting in significant risks include bleeding, infection, stroke, heart attack, arrhythmia, renal failure, adverse reactions to the anesthesia medications, as well as sudden death. When the valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Fully 2-5% of patients die during heart valve replacement surgery. The average hospital stay is between 1 to 2 weeks, with several more weeks to months required for complete recovery.

In recent years, advancements in "minimally-invasive" surgery and interventional cardiology have encouraged some investigators to pursue replacement of heart valves using remotely-implanted expandable valves without opening the chest or putting the patient on cardiopulmonary bypass. Various percutaneously- or surgically-delivered expandable valves are also being tested, primarily that use balloon- or self-expanding stents as anchors. For the purpose of inclusivity, the entire field will be denoted herein as the delivery and implantation of expandable valves. These valves typically include a scaffold or frame that expands radially outward into direct anchoring contact with the annulus, sometimes assisted with barbs.

For instance, Percutaneous Valve Technologies ("PVT") of Fort Lee, N.J. and Edwards Lifesciences of Irvine, Calif., have developed a balloon-expandable stent integrated with a bioprosthetic valve having flexible leaflets. The stent/valve device, marketed under the name Cribier-Edwards™ Aortic Percutaneous Heart Valve, is deployed across the native diseased valve to permanently hold the valve open, thereby alleviating a need to excise the native valve. The device is designed for percutaneous delivery in a cardiac catheterization laboratory under local anesthesia using fluoroscopic guidance, thereby avoiding general anesthesia and open-heart surgery.

The uniformity of contact between the expandable valve and surrounding annulus, with or without leaflets, should be such that no paravalvular leakage occurs, and therefore proper expansion is very important. Often, however, the highly calcified annulus in which the expandable valve implants is extremely uneven resulting in large gaps therebetween.

There remains a need for a prosthetic heart valve that can be surgically implanted in a more efficient procedure that reduces the time required on extracorporeal circulation, and there is also a need for an efficient means for implanting expandable prosthetic heart valves.

SUMMARY OF THE INVENTION

The present invention provides a non-expandable prosthetic heart valve for implantation at a heart valve annulus, comprising a non-expandable heart valve frame defining an orifice around an axis, a valve member, and an anchoring sleeve. The valve member includes at least one leaflet mounted to the frame and extending within the orifice operable to permit blood flow in one axial direction through the orifice and occlude flow in the opposite direction. The anchoring sleeve surrounds the frame and is at least partly made of a material that increases in size due to absorption of body fluids. Further, the anchoring sleeve is configured with sufficient mechanical strength to provide the primary means for anchoring the prosthetic heart valve to the annulus.

Desirably, the anchoring sleeve comprises an inner swellable material enclosed within a cover. The cover desirably restrains the inner swellable material from swelling to its maximum possible size. The swellable material may be selected from the group consisting of an isocyanate prepolymer, a polyol resin/polyether polyol, a hydrophilic acrylic resin base polymer, and a biocompatible hydrogel comprising at least one polysaccharide. Preferably, the swellable material is capable of swelling between 10-20 times its original size if unconstrained.

The anchoring sleeve may comprise a band that when swelled defines two axially spaced-apart flanges each surrounding the frame and a trough therebetween. For example, the anchoring sleeve comprises an inner swellable material enclosed within a flexible cover having a biased structure so as to be flexible in the regions adjacent the flanges but not therebetween so as to maintain a radial restraint and form the trough. In one embodiment, the non-expandable heart valve frame defines a nominal radius and the flanges extend radially outward from the trough by at least about 10-12% of the nominal radius. For example, the flanges extend radially outward by at least 3 mm from the trough.

Another aspect of the invention is an expandable prosthetic heart valve for implantation at a heart valve annulus. The expandable heart valve frame defines an orifice around an axis, and is convertible between a first, compressed state and a second, expanded state sized to contact a heart valve annulus. A valve member including at least one leaflet mounts to the frame and extends within the orifice. The valve member is operable to permit blood flow in one axial direction through the orifice and occlude flow in the opposite direction when the frame is in its second, expanded state. Finally, an anchoring sleeve surrounding a majority of the frame is at least partly made of a material that increases in size due to absorption of body fluids, the anchoring sleeve being configured with sufficient mechanical strength to assist the frame in anchoring the prosthetic heart valve to the annulus.

The expandable heart valve frame preferably defines a tubular shape in the second, expanded state, wherein the anchoring sleeve defines a generally tubular shape that extends axially nearly the entire length of the heart valve frame. Also, the anchoring sleeve when increased in size due to absorption of body fluids may define a generally tubular shape with a pair of axially spaced apart annular flanges. The expandable heart valve frame in the second, expanded state defines a nominal radius and the flanges desirably extend radially outward from the frame by at least about 10-12% of the nominal radius, or by at least 3 mm from the frame. The anchoring sleeve when increased in size due to absorption of body fluids may alternatively define a pair of axially spaced bulges and a trough therebetween in an hourglass configuration.

A method of anchoring a prosthetic heart valve to a heart valve annulus of the present invention comprises:

providing a prosthetic heart valve including a heart valve frame defining an orifice and a one-way valve member mounted to the frame and extending within the orifice, the prosthetic heart about further including an anchoring sleeve surrounding the frame at least partly made of a material that increases in size due to absorption of body fluids and being configured with sufficient mechanical strength to assist the frame in anchoring the prosthetic heart valve to the annulus; and delivering the prosthetic heart valve to a heart valve annulus and maintaining a desired position of the prosthetic heart valve long enough for the anchoring sleeve to increase in size from absorption of body fluids and anchor the prosthetic heart valve to the annulus.

In the aforementioned method, the annulus may be the aortic between the left ventricle and the aortic sinus cavities, wherein the valve is delivered in antegrade fashion from the apex of the left ventricle using an access catheter having a size of between about 30-50 French.

In one procedure the step of delivering comprises delivering the heart valve using a catheter over a guide wire, and either balloon expanding the prosthetic heart valve or permitting it to self-expand such that the sleeve contacts the annulus, and holding the heart valve in place for sufficient time for the anchoring sleeve to increase in size from absorption of body fluids and anchor the prosthetic heart valve to the annulus.

In another procedure the anchoring sleeve when increased in size due to absorption of body fluids defines a pair of axially spaced bulges and a trough therebetween in an hourglass configuration, and wherein the method includes positioning the trough over the target annulus to prevent migration of the valve. Also, the anchoring sleeve may change shape immediately upon being exposed to body fluid, and the method includes balloon expanding the heart valve to register the trough with the target annulus and outwardly compress the sleeve between the frame and the target annulus.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

Features and advantages of the present invention will become appreciated as the same become better understood with reference to the specification, claims, and appended drawings wherein:

DETAILED DESCRIPTION OF THE PREFERRED EMBODIMENTS

The present invention provides a suture-less means for attaching prosthetic heart valves to heart valve annuluses. Sutures are the most common technique for attaching conventional or non-expandable prosthetic heart valves, but their usage present some drawbacks, especially an increase in surgery time as indicated above. The primary means for attaching heart valves disclosed herein involves an anchoring sleeve which swells upon delivery to the implant location. A preferred embodiment features only the anchoring sleeve which, when expanded, provides a compression or interference fit between a valve support frame and the annulus. However, barbs or other automatically deploying anchoring elements may be used to supplement the function of the anchoring sleeve, and are not excluded by the term suture-less. The resulting implant procedure using the devices of the present invention is greatly speeded up from the omission of suturing.

The anchoring sleeve is at least partly made of a material that increases in size due to absorption of body fluids (i.e., blood). The anchoring sleeve is configured to have sufficient mechanical strength to at least assist the frame in anchoring the prosthetic heart valve to the annulus, and in some cases provide the primary anchoring means. Exemplary configurations for the anchoring sleeve will be provided below, but the preceding characterization excludes materials that have no real mechanical strength to anchor the heart valve to the annulus. For example, liquids or gels that are employed on the exterior of heart valves for various means may be hydrophilic and swell upon exposure to body fluids. However, these fluids are unable to add more than an incidental amount of anchorage to the existing mechanical anchoring structure of the heart valve. Therefore, the anchoring sleeve of the present invention is distinct from liquids or gels layered on the exterior of a prosthetic heart valve, unless they are designed to harden or cure to form flanges or ledges that help anchor the valve.

In the present application, a "non-expandable" prosthetic heart valve has a relatively dimensionally stable frame, but should not be interpreted to mean completely rigid, as some slight expansion of conventional "non-expandable" heart valves may be observed from a rise in temperature, for example, or other such incidental cause. Conversely, the term "expandable" stent or frame is used herein to refer to a component of a heart valve capable of expanding from a first, delivery diameter to a second, implantation diameter. An expandable structure, therefore, does not mean one that might merely undergo slight expansion.

As a point of further definition, the term "tissue anchoring member," or simply "anchoring member" refers to a structural component of a heart valve that is capable of attaching to tissue of a heart valve annulus. The anchoring members for expandable valves are most typically tubular stents, or stents having varying diameters. A stent is normally formed of a biocompatible metal wire frame, such as stainless steel, a non-ferromagnetic metal such as ELGILOY (a Co—Cr alloy), or Nitinol.

The term "valve member" refers to that component of a heart valve that possesses the fluid occluding surfaces to prevent blood flow in one direction while permitting it in another. As mentioned above, various constructions of valve members are available, including those with flexible leaflets and those with rigid leaflets or a ball and cage arrangement. The leaflets may be bioprosthetic, synthetic, or metallic.

The present application provides an anchoring sleeve that the swells upon contact with body fluid, or a predetermined time thereafter. The anchoring sleeve provides a primary means of anchoring conventional, non-expandable heart valves, and can be the primary means of anchoring expandable valves also. However, a preferred application of the anchoring sleeve for expandable valves is to supplement the existing anti-migration function of the expandable valve frame or stent. That is, the valve frame or stent expands to a particular diameter that is chosen to be slightly larger than the tissue orifice at the target annulus. Most prior expandable heart valves rely solely on the interference fit between the valve frame and the annulus to anchor the valve in place. Some expandable heart valves also include barbs or other such mechanical features that tend to pierce the surrounding tissue. Inclusion of the exemplary anchoring sleeve of the present invention around an expandable heart valve frame provides an additional level of interference to more securely hold the heart valve in place. Moreover, the anchoring sleeve compresses to a certain degree and thus conforms to the uneven annulus or calcified leaflets, further enhancing the ability to prevent migration of the valve. It is important to understand the distinction between the anchoring function of the anchoring sleeve in conventional versus expandable heart valves; the former being primary and the latter being either primary or supplemental.

FIGS. 1-4 illustrate an exemplary conventional, non-expandable heart valve 20 having an anchoring sleeve 22 around an inflow end thereof. The exemplary heart valve 20 is representative of all manners of non-expandable valves, but is particularly illustrated as one with three flexible leaflets 24 supported by three upstanding commissures 26. The commissures 26 project in the outflow direction and the valve features arcuate cusps 28 generally defining the periphery of each leaflet 24 between each two commissures. As shown, the anchoring sleeve 22 surrounds the inflow end of the valve 20 just below each of the cusps 28. This is the traditional placement of a suture-permeable sewing ring, but should not be considered to limit the relative placement of the anchoring sleeve 22.

Figure 2:
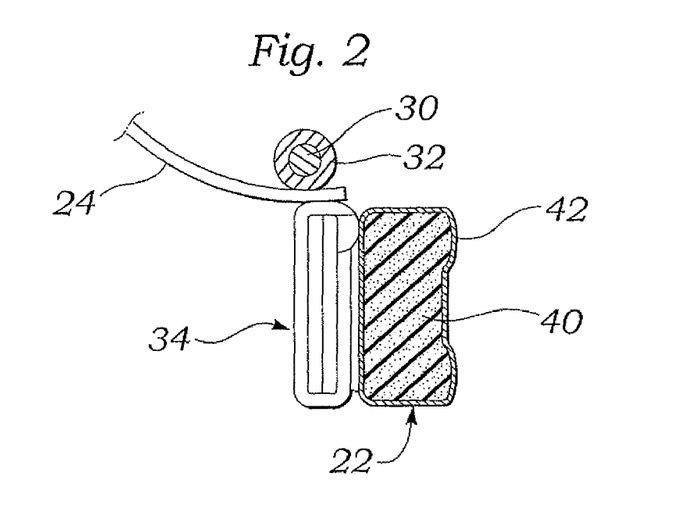
FIG. 2 is a radial cross-sectional view through one side of the inflow end of the prosthetic heart valve of FIG. 1.

An exemplary valve structure is schematically seen in cross-section in FIG. 2 through one of the cusps 28. The exemplary valve 20 includes an undulating wireform 30 having a fabric cover 32 that follows the upstanding commissures 36 and arcuate cusps 28. A cloth-covered stent structure 34 provides circumferential support at the inflow end of the valve 20, and is relatively dimensionally stable. Each of the flexible leaflets 24 is typically secured between the wireform 30 and stent structure 34. The anchoring sleeve 22 surrounds the stent structure 34 at the inflow end of the valve 20. Numerous designs for such flexible heart valves are suitable for use with the anchoring sleeve 22, and the preceding structural details of the valve should not be considered limiting. Moreover, as mentioned above, the anchoring sleeve 22 can be used on the exterior of mechanical valves too.

In the embodiment of FIGS. 1-4, the anchoring sleeve 22 comprises an inner swellable material 40 enclosed within a cover 42. The anchoring sleeve 22 is shown as generally annular and lying in a plane, although other designs might be slightly circumferentially undulating to follow the up-and-down anatomical shape of an aortic annulus. Also, although most conventional prosthetic heart valves have sewing rings that are uniform around their periphery, the anchoring sleeve 22 may be relatively larger (i.e., radially thicker or axially taller) in some areas. For example, the sewing ring disclosed in U.S. Patent Publication No. 2007/0016289, filed on Jul. 13, 2005, entitled "prosthetic Mitral Heart Valve Having a Contoured Sewing Ring," and expressly incorporated by reference herein, has at least one raised portion on its outflow edge to better match the contour of the mitral valve annulus. Those of skill in the art will understand that such bulges or other contours may be formed in vivo by a particular design of the shape changing anchoring sleeve 22.

Figure 1:
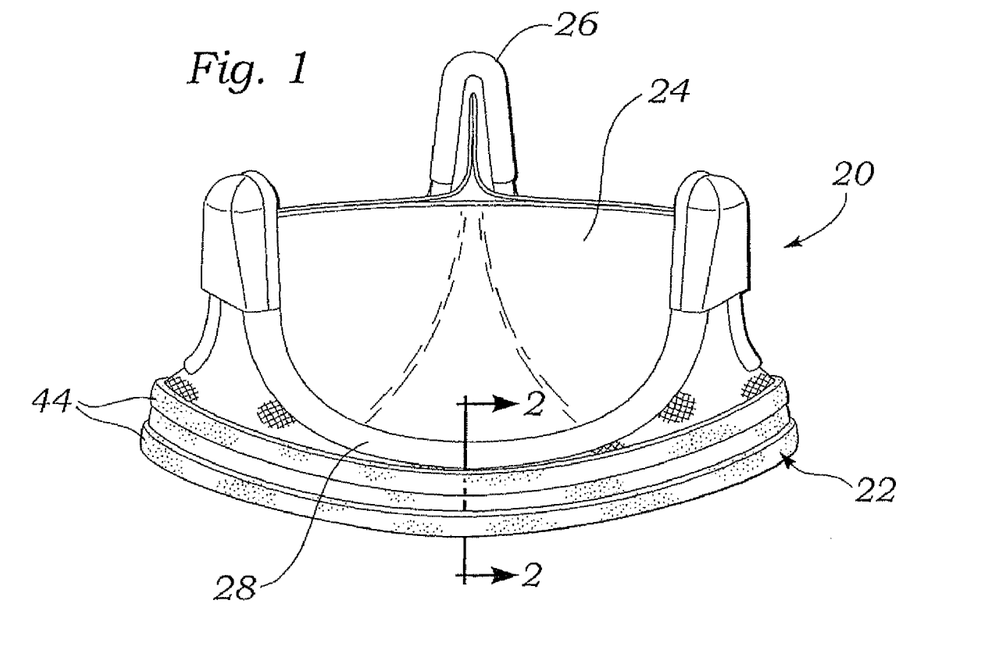
FIG. 1 is a perspective view of a non-expandable prosthetic heart valve having an anchoring sleeve of the present invention on an inflow end thereof.

With reference to FIGS. 1-2, the prosthetic heart valve 20 is shown in a configuration prior to implant, for example during storage. In this state, the anchoring sleeve 22 generally comprises a band with a substantially rectangular cross-section as seen in FIG. 2. Two axially spaced apart ribs 44 extend slightly radially outward. These ribs 44 eventually swell farther outward upon implant of the valve 20, as will be described below. Although they are shown as visible in FIGS. 1-2, the undeployed anchoring sleeve 22 may alternatively have a smooth or linear cross-section sectional outer surface.

Figure 3:
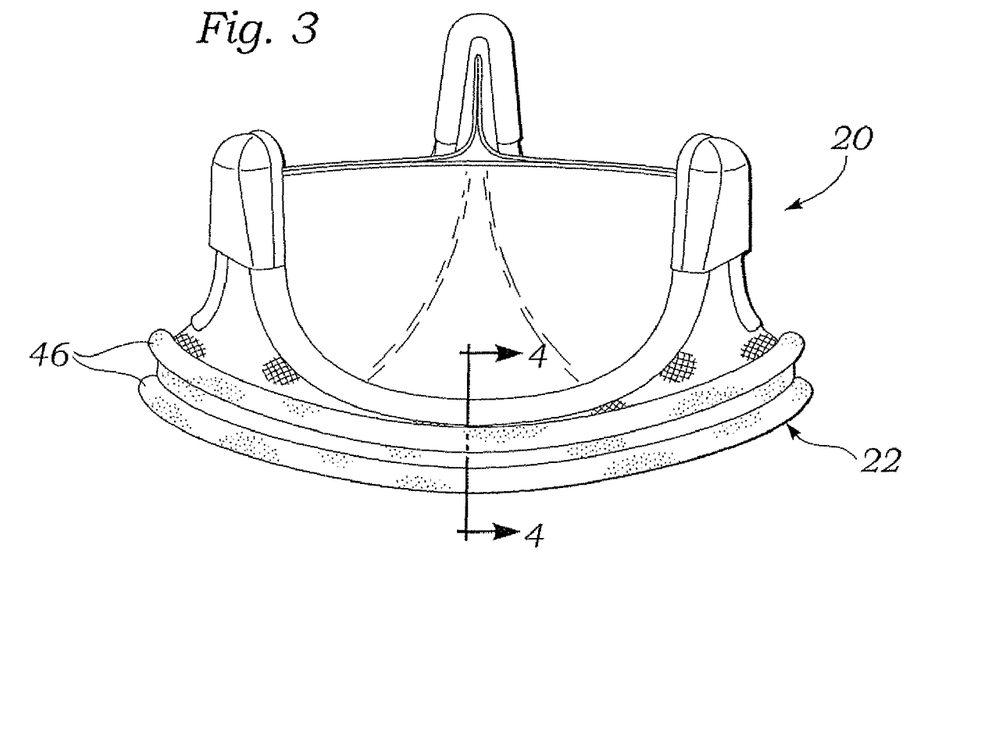
FIG. 3 is a perspective view of the prosthetic heart valve of FIG. 1 showing the anchoring sleeve in a deployed configuration.
Figure 4:
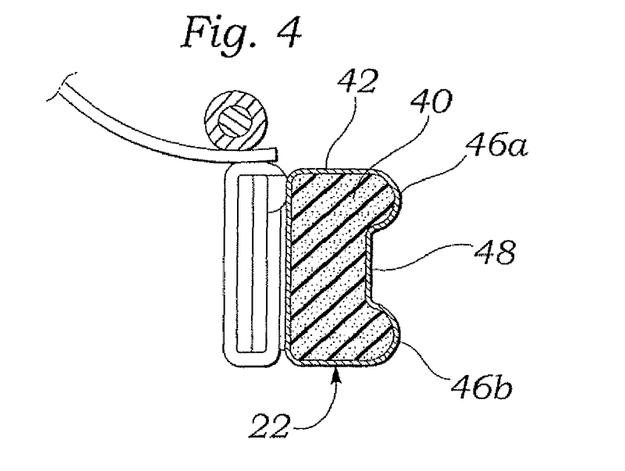
FIG. 4 is a radial cross-sectional view through one side of the inflow end of the prosthetic heart valve of FIG. 3.

FIGS. 3-4 show the heart valve 20 after the anchoring sleeve 22 has been deployed. As mentioned above, the anchoring sleeve 22 is formed at least partly by a swellable material 40 that increases in size. In the illustrated embodiment, the aforementioned ribs 44 enlarge in the radial direction to form two substantially larger flanges 46a, 46b, resembling O-rings. As seen in the view of FIG. 4, the cross-sectional shape of the anchoring sleeve 22 ultimately resembles the capital letter "B" with an annular groove or trough 48 created between the outflow flange 46*a* and the inflow flange 46*b*.

There are numerous ways to form the shape-changing or "self-inflating" anchoring sleeve 22 in addition to enclosing a swellable material 40 within a cover 42. In this primary configuration, however, the creation of the flanges 46 occurs by locating the swellable material in separate annular bands at the inflow and outflow edges of the anchoring sleeve 22 and a non-swellable material therebetween. Alternatively, or in addition to controlling the location of swelling of the swellable material 40, the cover 42 may have a biased design so as to be flexible in the regions adjacent the inflow and outflow edges, but not in the middle so as to maintain a radial restraint and form the trough 48.

Is important to understand that the deployed anchoring sleeve 22 has sufficient mechanical strength to assist in anchoring a prosthetic heart valve to the annulus. In the illustrated embodiment of FIGS. 1-4, the swellable material 40 in its deployed condition is relatively stiff such that the flanges 46*a*, 46*b* are capable of holding the valve within an annulus without sutures. The flanges 46 in this embodiment comprise the inner material 40 swelled outward and enclosed by the cover 42. The mechanical strength of the flanges 46 therefore is a combination of the physical properties of the inner material 40 after having swelled and the cover 42, in conjunction with their size and shape. In a preferred embodiment, the inner material 40 has the ability to swell to 10-20 times its original size upon exposure to blood and if unrestrained. The cover 42 desirably restrains the material 40 so that it swells outward and completely fills the cover, resulting in relatively firm flanges 46*a*, 46*b*. For example, the material 40 may be permitted by the size of the cover 42 to expand to only ½ of its maximum size.

Figure 5A:
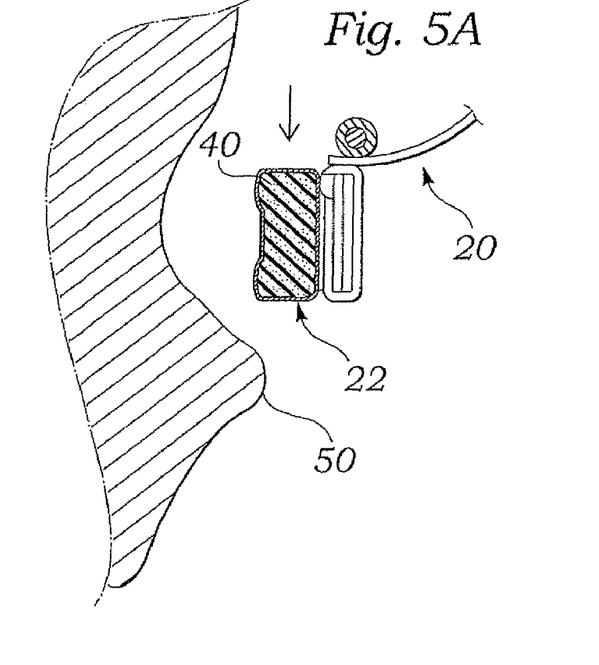
FIGS. 5A and 5B are sectional views through one side of an aortic annulus and surrounding anatomical structure showing two stages in the delivery and implant of the prosthetic heart valve of FIGS. 1-4.
Figure 5B:
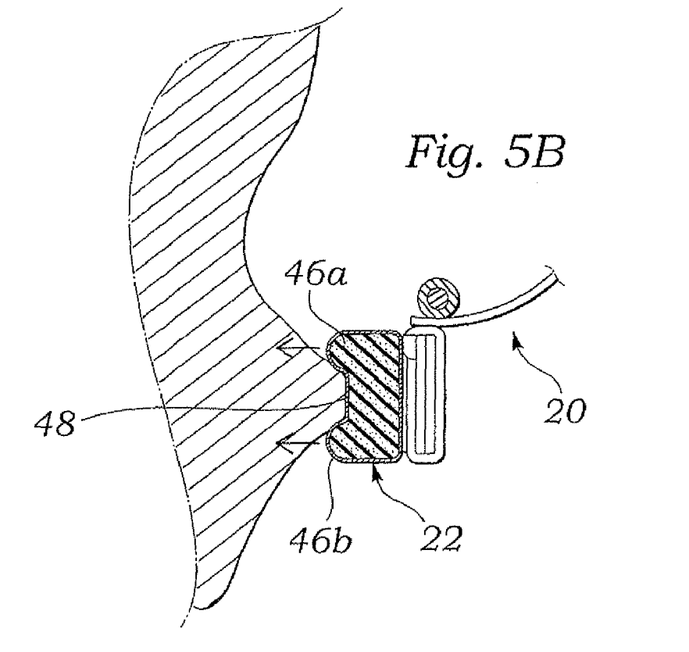

FIGS. 5A-5B schematically illustrate deployment of the valve 20 having the anchoring sleeve 22. FIG. 5A shows the valve 20 being delivered toward a heart valve annulus 50, in this case the aortic annulus. It should be noted that in a conventional surgery to implant a non-expandable heart valve, the native leaflets are typically removed and the annulus 50 sculpted to receive the valve. The annulus 50 comprises a relatively fibrous inwardly-directed ledge against which the heart valve 20 may be implanted. As illustrated, the outer diameter of the anchoring sleeve 22 is relatively larger than the sculpted annulus 50. The surgeon will select the properly sized valve accordingly. In a preferred embodiment, the anchoring sleeve 22 comprises a swellable material 40 that expands upon contact with body fluid. Preferably, however, the material 40 does not immediately expand but instead exhibits a delayed expansion so as to permit delivery and placement at the annulus without difficulty. This is not unusual because of the time required to absorb fluid.

Ultimately, the surgeon positions the valve 20 immediately adjacent the annular ledge 50 and maintains the position long enough for the anchoring sleeve 22 to fully deploy. In this case, the outflow and inflow flanges 46*a*, 46*b* swell outward to project above and below the annular ledge 50, with the ledge positioned in the trough 48. Again, it should be mentioned that the annular ledge 50 for the aortic annulus may be slightly undulating or scalloped as it follows the native commissures and cusps to which the excised leaflets previously attached. To provide a more secure anchoring contact between the valve and annulus, therefore, the anchoring sleeve 22 may be similarly scalloped. In such a non-planar embodiment the surgeon must rotate the prosthetic heart valve 20 to align the undulations in the valve with the undulations in the annular ledge 50.

The relative change in radial dimension of the anchoring sleeve 22 must be sufficient to hold the heart valve 20 in place once implanted, preventing migration. In a preferred embodiment, the flanges 46 extend radially outward by at least 3 mm from the trough 48. Stated another way, the flanges 46 extend radially outward by at least about 10-12% of the nominal radius of the valve 20. Prosthetic heart valves are conventionally sized in odd increments of 2 mm starting in 19 mm (i.e., 19, 21, 25, etc.), denoting the outer diameter of the main structural component of the valve that defines the flow orifice. Therefore, a 21 mm valve has a nominal radius of 10.5 mm, and the flanges 46 therefore extend radially outward by at least about 2 mm. Furthermore, in a preferred embodiment the flanges 46 once expanded are spaced apart by about 4 mm.

Figure 6:
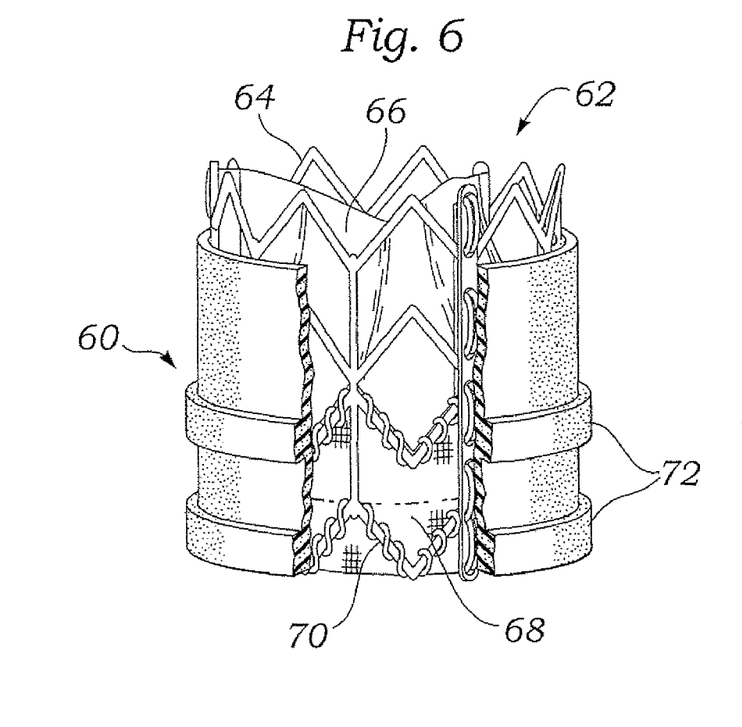
FIG. 6 is a perspective view of an expandable prosthetic heart valve having an anchoring sleeve of the present invention thereon.
Figure 7:
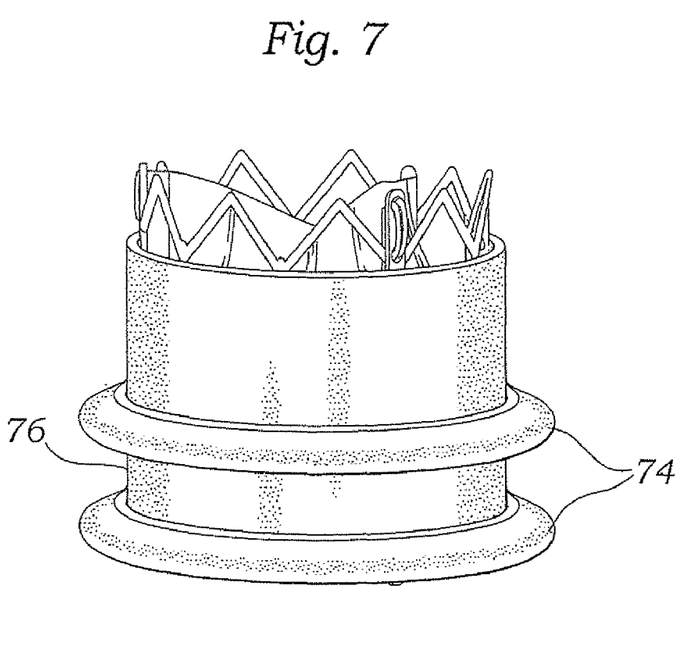
FIG. 7 is a perspective view of the prosthetic heart valve of FIG. 6 showing the anchoring sleeve in a deployed configuration.

Now with reference to FIGS. 6-7, an anchoring sleeve 60 of the present invention for use with an expandable prosthetic heart valve 62 is shown. The exemplary heart valve 62 comprises a plurality of struts 64 arranged axially and at angles around the circumference to define a tubular frame when expanded. Flexible leaflets 66 attach to the frame via a fabric interface 68 and a plurality of sutures 70. Again, the expandable heart valve 62 shown is exemplary only, and other designs will benefit from the addition of the anchoring sleeve 60. These expandable heart valves typically have an expandable frame as shown with flexible occluding leaflets therewithin. In the prior art, the self- or balloon-expandable frames anchor to the surrounding annulus through a simple interference fit, barbs, or a particular contour of the frame which provides top and bottom flanges. There are numerous such designs that provide an inherent anchoring capacity, and it should be understood that the anchoring sleeve 60 may be the primary mechanical anchorage or may just assist the frame in preventing migration of the valve.

In this embodiment, the anchoring sleeve 60 defines a generally tubular shape that extends axially nearly the entire length of the heart valve 62 and therefore surrounds a majority thereof. A pair of spaced apart annular ribs 72 shown in FIG. 6 shape change into annular flanges 74 as seen in FIG. 7 upon implant in the body. More particularly, the anchoring sleeve 60, or just the portion at the ribs 72, is made at least partly of the material that swells upon contact with body fluids (i.e., blood). For example, the portion of the anchoring sleeve 60 encompassing the ribs 72 may be constructed in a like manner as the anchoring sleeve 22 of FIGS. 1-5.

As seen in FIG. 7, one of the expanded flanges 74 surrounds an inflow end of the prosthetic heart valve 62, while the second flange is axially spaced therefrom. The position of the flanges 74 desirably conforms to the particular target annulus, such that a narrow ledge of the annulus fits within a trough 76 between the flanges. Again, the size, shape, and spacing of the flanges 74 can be modified to conform to different annuluses (e.g., scalloped), or for the different pathologies (e.g., greater calcification).

Figures 8, 9A, 9B:
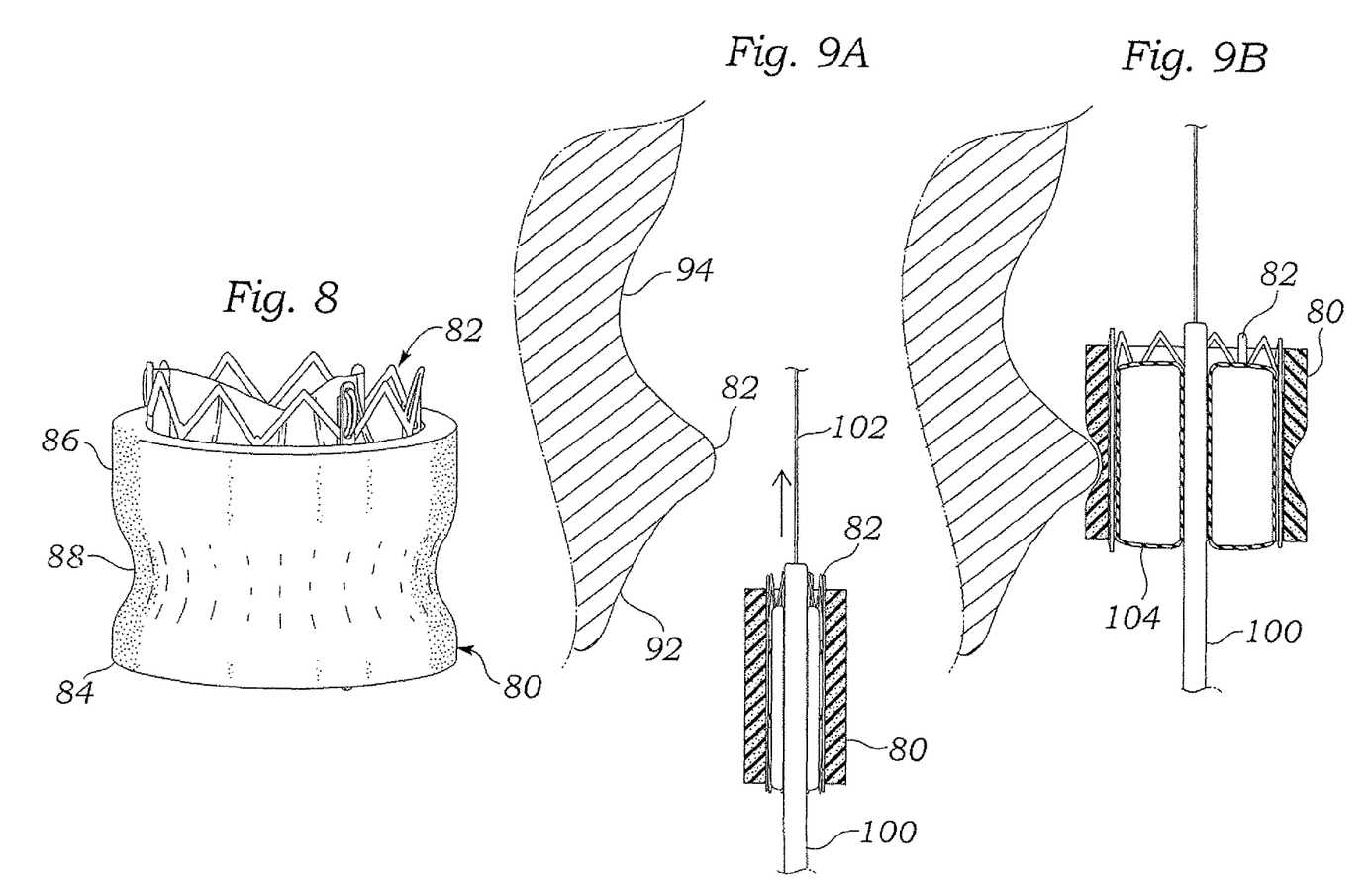
FIG. 8 is a perspective view of an expandable prosthetic heart valve having an alternative anchoring sleeve of the present invention thereon.
FIGS. 9A and 9B are sectional views through one side of an aortic annulus and surrounding anatomical structure showing two stages in the delivery and implant of the prosthetic heart valve of FIG. 8.

FIG. 8 illustrates an alternative anchoring sleeve 80 for use with an expandable prosthetic heart valve 82. The heart valve 82 may have the same construction as the heart valve 62 of FIGS. 6-7, or any other design with an expandable frame and occluding leaflets therewithin. The anchoring sleeve 80 covers a majority of the exterior of the prosthetic heart valve 82, and is shown in its deployed configuration in FIG. 8. The exterior surface of the anchoring sleeve 80 has an inflow bulge 84, an outflow bulge 86, and a depression or trough 88 therebetween. The radial proportions of the bulges 84, 86 may be similar to those described above with respect to the flanges 46 of the anchoring sleeve 22 of the first embodiment. The contour resembles an hourglass. This contour is designed to receive the target annulus within the trough 88 and prevent migration of the valve 82. As before, the anchoring sleeve 80 is made at least partly of a material that swells upon implant.

FIGS. 9A and 9B illustrate two steps in a procedure for implanting the prosthetic heart valve 82 having the anchoring sleeve 80 thereon. In this sequence, the annulus 90 is the aortic between the left ventricle 92 and the aortic sinus cavities 94, and the valve is introduced in antegrade fashion from the apex of the left ventricle. A catheter 100 carrying the heart valve 82 advances over a guide wire 102. When in position adjacent the annulus 90, a balloon 104 carried by the catheter 100 inflates, thus outwardly expanding the prosthetic heart valve 82 and anchoring sleeve 80 thereon. Alternatively, the heart valve 82 may be a self-expanding type which is carried within a sleeve and ejected therefrom at the annulus 90. Preferably, the valve frame expands sufficiently such that it would contact the annulus even in the absence of the sleeve 80.

The anchoring sleeve 80 is seen in cross-section in FIG. 9A to have a uniform or cylindrical outer profile during delivery. It is not until a predetermined time after implant in the body that the exterior contour seen in FIG. 9B appears from absorption of fluid. It is further conceivable that the balloon 104 may be expanded to outwardly compress the heart valve 82 against the annulus 90 prior to shape change of anchoring sleeve 80. Soon thereafter or over time, the inflow bulge 84 and outflow bulge 86 form to help maintain the proper position of the prosthetic heart valve, and the trough 88 is positioned over the target annulus to prevent migration of the valve 82. Alternatively the anchoring sleeve 80 changes shape immediately upon being exposed to body fluid, there being no need to maintain a small profile to fit the compressed valve 82 into the annulus 90.

One particularly useful application for the anchoring sleeves of the present invention is in the relatively recent transapical delivery technique shown in FIGS. 9A and 9B. In this technique, a relatively large access tube or cannula passes through the apex of the left ventricle, and the balloon catheter carrying the prosthetic heart valve passes therethrough. In contrast to a percutaneous delivery route through the vasculature, which limits the access catheter size to about 20 French, the size of the access cannula may be up to 50 French, preferably between about 30-50 French. A relatively thick anchoring sleeve 80 may therefore be added to the prosthetic heart valve 82 without exceeding surgical constraints.

A number of materials are suitable for use as the swellable material 40. Two such materials are isocyanate prepolymer and polyol resin/polyether polyol. Another potential material is called Hydron (trademark of National Patent Development Corporation, New York, N.Y.), a hydrophilic acrylic resin base polymer disclosed in U.S. Pat. No. 3,975,350, expressly incorporated by reference herein. Other swellable materials suitable for use as the material 40 comprise biocompatible hydrogels having at least one polysaccharide, as disclosed in U.S. Patent Application No. 2005/0220882, also expressly incorporated by reference herein.

The cover 42 may be a knit polyester fabric about 0.2 mm thick biased so as to be flexible in the regions adjacent the inflow and outflow edges, but not in the middle so as to maintain a radial restraint and form the trough 48. Alternatively, potential encapsulating/encasing materials for the cover 42 could be pericardium (various animals) or polymer (e.g., polyurethane, mylar, carbon nano-tube sheets).

While the invention has been described in its preferred embodiments, it is to be understood that the words which have been used are words of description and not of limitation. Therefore, changes may be made within the appended claims without departing from the true scope of the invention.

What is claimed is:

1. A non-expandable prosthetic heart valve for implantation at a heart valve annulus, comprising:
    a non-expandable heart valve frame defining an orifice around an axis;
    a valve member including at least one leaflet mounted to the frame and extending within the orifice, the valve member being operable to permit blood flow in one axial direction through the orifice and occlude flow in the opposite direction; and
    two axially spaced-apart flanges each surrounding the frame each at least partly made of a material that increases in size due to absorption of body fluids, wherein the flanges are configured with sufficient mechanical strength to provide the primary means for anchoring the prosthetic heart valve to the annulus, wherein each of the flanges comprises an inner swellable material enclosed within a cover.

2. The heart valve of claim 1, wherein the two axially spaced-apart flanges are provided on a single anchoring sleeve that surrounds the frame with a trough between the flanges.

3. The heart valve of claim 1, wherein the swellable material is selected from the group consisting of:
    an isocyanate prepolymer,
    a polyol resin/polyether polyol,
    a hydrophilic acrylic resin base polymer, and
    a biocompatible hydrogel comprising at least one polysaccharide.

4. The heart valve of claim 1, wherein the swellable material is capable of swelling between 10-20 times its original size if unconstrained.

5. The heart valve of claim 1, wherein the flexible cover has a biased structure so as to be flexible in the regions adjacent the flanges but not therebetween so as to maintain a radial restraint and form the trough.

6. The heart valve of claim 1, wherein the non-expandable heart valve frame defines a nominal radius and the flanges extend radially outward therefrom by at least about 10-12% of the nominal radius.

7. The heart valve of claim 6, wherein the flanges extend radially outward at least 3 mm from the nominal radius.

8. An expandable prosthetic heart valve for implantation at a heart valve annulus, comprising:
    an expandable heart valve frame defining an orifice around an axis, the frame being convertible between a first, compressed state and a second, expanded state sized to contact a heart valve annulus;
    a valve member including at least one leaflet mounted to the frame and extending within the orifice, wherein the valve member permits blood flow in one axial direction through the orifice and occludes flow in the opposite direction when the frame is in its second, expanded state; and
    a pair of axially spaced apart annular flanges surrounding the frame each at least partly made of a material that increases in size due to absorption of body fluids, wherein the flanges are configured with sufficient mechanical strength to assist the frame in anchoring the prosthetic heart valve to the annulus, wherein the expandable heart valve frame in the second, expanded state defines a nominal radius and the flanges extend radially outward from the frame by at least about 10-12% of the nominal radius.

9. The heart valve of claim 8, wherein the annular flanges are formed on a single anchoring sleeve.

10. The heart valve of claim 9, wherein the expandable heart valve frame defines a tubular shape in the second, expanded state, and wherein the anchoring sleeve defines a generally tubular shape that extends axially nearly the entire length of the heart valve frame.

11. The heart valve of claim 9, wherein the annular flanges are separated by a trough defining an hourglass configuration.

12. The heart valve of claim 8, wherein the expandable heart valve frame in the second, expanded state defines a nominal radius and the flanges extend radially outward by at least 3 mm from the nominal radius.

13. A method of anchoring a prosthetic heart valve to a heart valve annulus, comprising:
   providing a prosthetic heart valve including a heart valve frame defining an orifice and a one-way valve member mounted to the frame and extending within the orifice, the prosthetic heart valve further including pair of axially spaced ribs surrounding the frame each at least partly made of a material that increases in size due to absorption of body fluids and being configured with sufficient mechanical strength to assist the frame in anchoring the prosthetic heart valve to the annulus, the ribs each comprising an inner swellable material enclosed within a cover; and
   delivering the prosthetic heart valve to a heart valve annulus and maintaining a desired position of the prosthetic heart valve long enough for the pair of axially spaced ribs to increase in size from absorption of body fluids and anchor the prosthetic heart valve to the annulus.

14. The method of claim 13, wherein the annulus is the aortic annulus between the left ventricle and the aortic sinus cavities, and the valve is delivered in antegrade fashion from the apex of the left ventricle using an access catheter having a size of between about 30-50 French.

15. The method of claim 13, wherein the axially spaced ribs are formed on a single anchoring sleeve including a trough therebetween in an hourglass configuration, and wherein the method includes positioning the trough over the target annulus to prevent migration of the valve.

16. The method of claim 15, wherein the step of delivering comprises delivering the heart valve using a catheter over a guide wire, and either balloon expanding the prosthetic heart valve or permitting it to self-expand such that the sleeve contacts the annulus, and holding the heart valve in place for sufficient time for the anchoring sleeve to increase in size from absorption of body fluids and anchor the prosthetic heart valve to the annulus.

17. The method of claim 15, wherein the anchoring sleeve changes shape immediately upon being exposed to body fluid, and the method includes balloon expanding the heart valve to register the trough with the target annulus and outwardly compress the sleeve between the frame and the target annulus.

18. A non-expandable prosthetic heart valve for implantation at a heart valve annulus, comprising:
   a non-expandable heart valve frame defining an orifice around an axis;
   a valve member including at least one leaflet mounted to the frame and extending within the orifice, the valve member being operable to permit blood flow in one axial direction through the orifice and occlude flow in the opposite direction; and
   two axially spaced-apart flanges each surrounding the frame each at least partly made of a material that increases in size due to absorption of body fluids, wherein the flanges are configured with sufficient mechanical strength to provide the primary means for anchoring the prosthetic heart valve to the annulus, wherein the non-expandable heart valve frame defines a nominal radius and the flanges extend radially outward therefrom by at least about 10-12% of the nominal radius.

19. The heart valve of claim 18, wherein the flanges extend radially outward at least 3 mm from the nominal radius.

20. The heart valve of claim 18, wherein each of the flanges comprises an inner swellable material enclosed within a cover.

21. The heart valve of claim 20, wherein the swellable material is capable of swelling between 10-20 times its original size if unconstrained.

22. An expandable prosthetic heart valve for implantation at a heart valve annulus, comprising:
   an expandable heart valve frame defining an orifice around an axis, the frame being convertible between a first, compressed state and a second, expanded state sized to contact a heart valve annulus;
   a valve member including at least one leaflet mounted to the frame and extending within the orifice, wherein the valve member permits blood flow in one axial direction through the orifice and occludes flow in the opposite direction when the frame is in its second, expanded state; and
   a pair of axially spaced apart annular flanges surrounding the frame each at least partly made of a material that increases in size due to absorption of body fluids, wherein the flanges are configured with sufficient mechanical strength to assist the frame in anchoring the prosthetic heart valve to the annulus, wherein the expandable heart valve frame in the second, expanded state defines a nominal radius and the flanges extend radially outward by at least 3 mm from the nominal radius.

23. The heart valve of claim 22, wherein the annular flanges are formed on a single anchoring sleeve.

24. The heart valve of claim 23, wherein the expandable heart valve frame defines a tubular shape in the second, expanded state, and wherein the anchoring sleeve defines a generally tubular shape that extends axially nearly the entire length of the heart valve frame.

25. The heart valve of claim 23, wherein the annular flanges are separated by a trough defining an hourglass configuration.

* * * * *